US012420030B2

(12) United States Patent
Bruns et al.

(10) Patent No.: US 12,420,030 B2
(45) Date of Patent: Sep. 23, 2025

(54) PEN NEEDLE

(71) Applicant: Owen Mumford Limited, Woodstock (GB)

(72) Inventors: Robert Bruns, Woodstock (GB); Myles Whiting, Woodstock (GB)

(73) Assignee: OWEN MUMFORD LIMITED, Oxfordshire (GB)

(*) Notice: Subject to any disclaimer, the term of this patent is extended or adjusted under 35 U.S.C. 154(b) by 881 days.

(21) Appl. No.: 17/609,506

(22) PCT Filed: May 21, 2020

(86) PCT No.: PCT/EP2020/064221
§ 371 (c)(1),
(2) Date: Nov. 8, 2021

(87) PCT Pub. No.: WO2020/229706
PCT Pub. Date: Nov. 19, 2020

(65) Prior Publication Data
US 2022/0233783 A1 Jul. 28, 2022

(30) Foreign Application Priority Data
May 16, 2019 (GB) ................................... 1906918

(51) Int. Cl.
*A61M 5/32* (2006.01)
(52) U.S. Cl.
CPC ............ *A61M 5/3243* (2013.01); *A61M 5/32* (2013.01); *A61M 5/3205* (2013.01);
(Continued)
(58) Field of Classification Search
CPC .. A61M 2005/3246; A61M 2005/3247; A61M 2005/3254; A61M 2005/3261;
(Continued)

(56) References Cited

U.S. PATENT DOCUMENTS 7,384,414 B1 * 6/2008 Marshall ............... A61M 5/347
604/198
7,462,168 B2 * 12/2008 Stonehouse ......... A61M 5/3272
604/198
2014/0107586 A1 4/2014 Ruan et al.

FOREIGN PATENT DOCUMENTS

EP 1949928 A1 7/2008
EP 1949929 A1 7/2008
(Continued)

OTHER PUBLICATIONS

International Search Report and Written Opinion of the International Searching Authority from corresponding PCT Application No. PCT/EP2020/064221 dated Jul. 7, 2020 (12 pages).

*Primary Examiner* — Shefali D Patel
(74) *Attorney, Agent, or Firm* — QUARLES & BRADY LLP

(57) ABSTRACT

A pen needle and a method of using the pen needle. The pen needle includes a housing, a needle carrier in the housing supporting a needle, a distal shroud positioned around the needle within the housing, a distal compression spring positioned around the needle between the needle carrier and the distal shroud, a proximal shroud positioned around the needle within the housing, and a proximal compression spring positioned around the needle between the needle and the proximal shroud. The proximal shroud is movable between a first position, in which the proximal shroud engages the distal shroud to hold the distal shroud in engagement with the housing, and a second position in which the proximal shroud is disengaged from the distal shroud allowing the distal shroud to move in a distal direction to project from the housing and surround a distal end of the needle.

19 Claims, 14 Drawing Sheets

(52) U.S. Cl.
CPC .......... *A61M 5/321* (2013.01); *A61M 5/3245* (2013.01); *A61M 2005/3254* (2013.01)

(58) Field of Classification Search
CPC .. A61M 2005/3263; A61M 2005/3264; A61M 2005/3267; A61M 2205/0216; A61M 2205/27; A61M 2205/273; A61M 5/32; A61M 5/3202; A61M 5/3204; A61M 5/3205; A61M 5/321; A61M 5/3243; A61M 5/3245; A61M 5/3257; A61M 5/326; A61M 5/3271; A61M 5/3272; A61M 5/3275; A61M 5/50
See application file for complete search history.

(56) References Cited

FOREIGN PATENT DOCUMENTS

| | | |
|---|---|---|
| WO | 2009102612 A1 | 8/2009 |
| WO | 2016181127 A1 | 11/2016 |

\* cited by examiner

PEN NEEDLE

CROSS-REFERENCE TO RELATED APPLICATIONS

The present application represents the United States National Stage of International Application No. PCT/EP2020/064221, filed May 21, 2020, which claims priority to British Patent Application Serial No. GB 1906918.6, filed May 16, 2019, and entitled, "PEN NEEDLE," all of which are incorporated herein by reference in their entirety.

TECHNICAL FIELD

This invention relates to a pen needle device and to a method of using such a device. The pen needle devices may be useful as a single-use disposable needle device such as are typically configured for attachment to an injection device, cartridge or syringe.

BACKGROUND ART

Injection devices are commonly used by patients to self-administer injections of medicament such as insulin. Such devices are typically provided in a pen-like body which contains a syringe cartridge of medicament and a delivery mechanism which is arranged to dispense the medicament via a needle in response to a user pressing a button or trigger.

As such injection devices can be either reusable, either by replacing the cartridge of medicament or by delivering multiple separate injections until the medicament within the device has been fully consumed, it is common to arrange the device to receive a disposable, single-use, needle device. Such needle devices are generally referred to as "pen needles".

Pen needles comprise a body or hub which is configured to be attached to the injection device in use (for example by means of a screw thread) and which supports the needle. Typically, the needle is a double ended needle having a forward (distal) end for use in penetrating the skin of a user, and a rearward (proximal) end which pierces a septum of the cartridge in the injection device when the pen needle is attached to the device.

It is known to provide pen needles with a shroud which is arranged to cover the needle after use to reduce the risk of accidental needle-stick injuries after use or during disposal of the needle device. An example of such a device is the BD AutoShield Duo Pen Needle available from Becton Dickinson (www.bd.com)

EP 1949928 A (BECTON DICKINSON CO) 30 Jul. 2008 discloses a pen needle in which the needle retracts inside the hub after use. EP 1949929 A (BECTON DICKINSON CO) 30 Jul. 2008 discloses a pen needle with both injection and non-injection end shields.

WO 2009/102612 May 2, 2009 (Becton, Dickinson and Company) discloses a pen needle with a spring-loaded shield that can be deployed by operation of a button.

WO 2016/181127 A (OWEN MUMFORD LTD) 17 Nov. 2016 discloses a pen needle with a manually operable shield that allows both the forward and reward parts of the needle to be covered after use.

Some pen needle devices have spring-loaded shields that can be automatically activated when the needle is withdrawn from the injection site. However, problems can occur if the shield deploys before the injection is complete, leading to injection of less than the desired amount of medicament, or the deposit of medicament on the surface of the skin.

This invention aims to address at least some of the problems encountered with the deployment of shields or shrouds in previous pen needle devices.

SUMMARY OF INVENTION

The invention provides a pen needle comprising:
 a housing defining a central cavity with a distal end having a distal opening and a proximal end having a proximal opening;
 a needle carrier located within the central cavity and supporting a needle that extends through the central cavity such that a distal end of the needle projects from the distal end of the cavity through the distal opening;
 a distal shroud positioned around the needle and located within the central cavity at the distal end, the distal shroud including formations that, when engaged with the housing, limit axial movement of the distal shroud in a distal direction;
 a distal compression spring positioned around the needle and located between the needle carrier and the distal shroud, wherein the compression spring acts to urge the distal shroud away from the needle carrier towards the distal opening; and
 a proximal member located within the central cavity at the proximal end;
 wherein the proximal member is movable in use between a first position, in which a distal end of the proximal member engages a proximal end of the distal shroud to hold the formations in engagement with the housing, and a second position in which the proximal member is closer to the proximal opening and the distal end of the proximal member is not engaged with the proximal end of the distal shroud such that the formations are movable out of engagement with the housing and the distal shroud is movable in a distal direction by the distal compression spring to project from the distal opening and to surround the distal end of the needle projecting from the distal opening.

The invention also provides a method of using the pen needle, comprising:
 with the proximal member in the first position, connecting a cartridge housing to the proximal end of the housing so as to engage the proximal end of the proximal member; and
 disconnecting the cartridge housing from the proximal end of the housing, thereby releasing the proximal member so as to disengage the distal end of the proximal member from the proximal end of the distal shroud thereby releasing the formations to move out of engagement with the housing and moving the distal shroud in a distal direction by the distal compression spring to project from the distal opening and to surround the distal end of the needle projecting from the distal opening.

The proximal end of the housing can have formations for connecting a cartridge housing to the pen needle, wherein, when connected, the cartridge housing holds the proximal member in the first position, and when disconnected, allows the proximal member to move to the second position.

The proximal member can comprise a proximal shroud positioned around the needle and located within the central cavity at the proximal end. The pen needle can further comprise a proximal compression spring positioned around the needle and located between the needle and the proximal shroud, wherein the proximal compression spring acts to urge the proximal shroud away from the needle carrier towards the proximal opening; wherein the proximal shroud is movable by the proximal compression spring between the first position and the second position. A proximal compression spring can be positioned around the needle and located between the needle and the proximal shroud, wherein the proximal compression spring acts to urge the proximal shroud away from the needle carrier towards the proximal opening;

By arranging the proximal shroud to engage the distal shroud and hold it in engagement with the housing, deployment of the distal shroud can be controlled to take place after the proximal shroud has deployed to shroud the proximal end of the needle. In this way the likelihood of early activation of the distal shroud can be reduced.

The distal end of the proximal shroud can engage in the proximal end of the distal shroud in the first position to hold the formations in engagement with the housing. In the second position, the distal end of the proximal shroud is not engaged in the proximal end of the distal shroud such that the formations are movable out of engagement with the housing.

The formations on the distal shroud can comprise deformable formations having ramped external surfaces that are engageable with corresponding ramped internal surfaces on the housing; the action of the distal compression spring causing the deformable formations to deform and disengage from the formations in the housing when the distal end of the proximal shroud is disengaged from the proximal end of the distal shroud.

The distal shroud can comprise further formations that are engageable with distal end formations in the housing to prevent disengagement of the distal shroud from the housing when moved in a distal direction by the distal compression spring to project from the distal opening and to surround the distal end of the needle projecting from the distal opening.

The proximal end of the needle can be located within the proximal shroud when the proximal shroud is in the second position. In the first position of the proximal shroud, the proximal end of the needle can project beyond the proximal end of the proximal shroud by a length that is less than the length of the distal end of the proximal shroud engaged with the proximal end of the distal shroud.

The proximal shroud can include a latch for holding it in the second position.

The proximal shroud can comprise an actuator plate at its proximal end by which force can be applied to the proximal shroud to rotate it within the housing and to move it axially against the proximal compression spring.

The proximal shroud can engage the needle carrier by means of a pin and track arrangement, such that rotation of the proximal shroud relative to the needle carrier moves the pin from a first track portion in which the proximal shroud is held in the first position against the proximal compression spring, to a second track portion in which the proximal shroud is axially movable to the second position by the proximal compression spring. The pin and track arrangement can comprise a pin on an outer surface of the proximal shroud and a track formed in a wall of the needle carrier. The track in the wall of the carrier can comprise a pin seat defining the first track portion, and a transition channel extending axially and azimuthally along the wall of the carrier from the first track portion to the second track portion extending axially along the wall of the carrier. The track can further comprise an assembly channel extending axially along the carrier wall to connect to the transition channel on the opposite side of the pin seat to the second track portion.

The proximal opening of the housing can include an internal screw thread by means of which a cartridge housing can be attached, such that screwing the cartridge housing onto the housing applies axial and rotational force to the actuator plate.

The housing can include internal formations that engage the needle carrier to locate it axially and rotationally.

The method can comprise:
 with the proximal shroud in the first position, connecting a cartridge housing to the proximal end of the housing so as to engage the proximal end of the proximal shroud and to rotate the proximal shroud in the housing and move it axially against the proximal compression spring; and
 disconnecting the cartridge housing from the proximal end of the housing, thereby releasing the proximal compression spring so as to move the proximal housing to the second position to initially surround the proximal end of the spring, and to subsequently disengage the distal end of the proximal shroud from the proximal end of the distal shroud, thereby releasing the formations to move out of engagement with the housing so as to move the distal shroud in a distal direction by the distal compression spring to project from the distal opening and to surround the distal end of the needle projecting from the distal opening.

DESCRIPTION OF EMBODIMENTS

Figure 1:
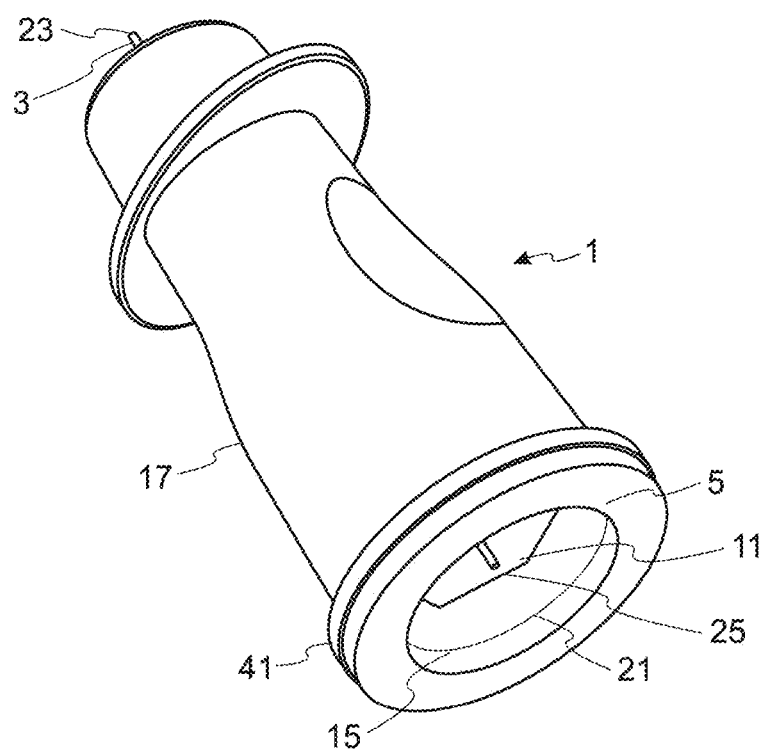
FIG. 1 is a perspective view of a pen needle in a pre-use state, viewed from the proximal end.
Figure 2:
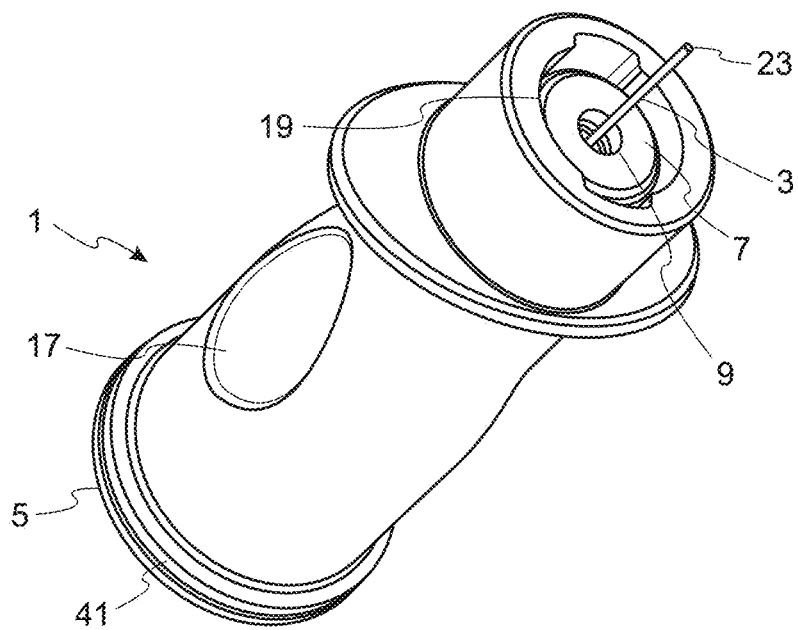
FIG. 2 is a perspective view of the pen needle of FIG. 1, viewed from the distal end.
Figure 3:
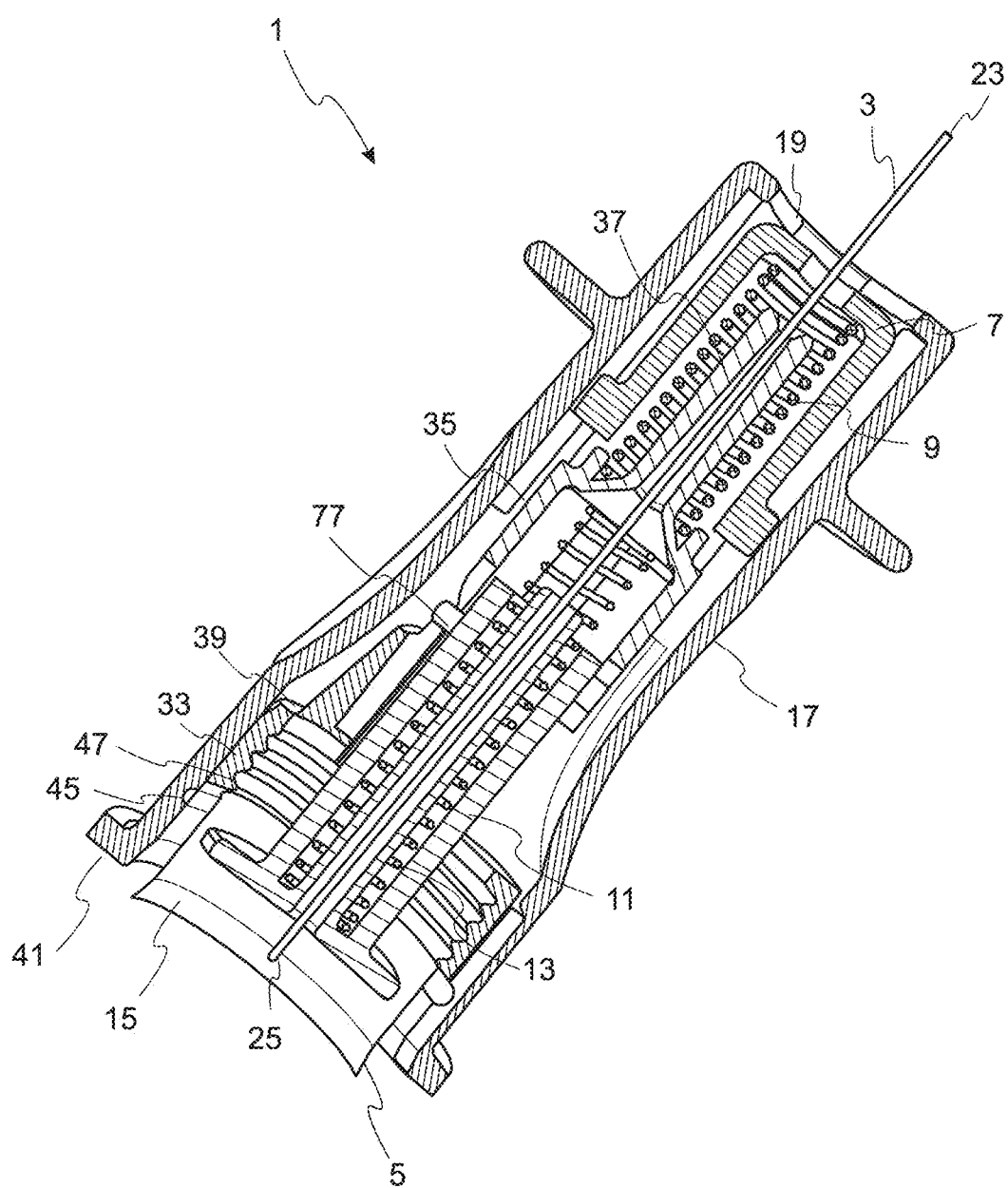
FIG. 3 is a cross-sectional view of the pen needle of FIG. 1 in a pre-use state.
Figure 4:
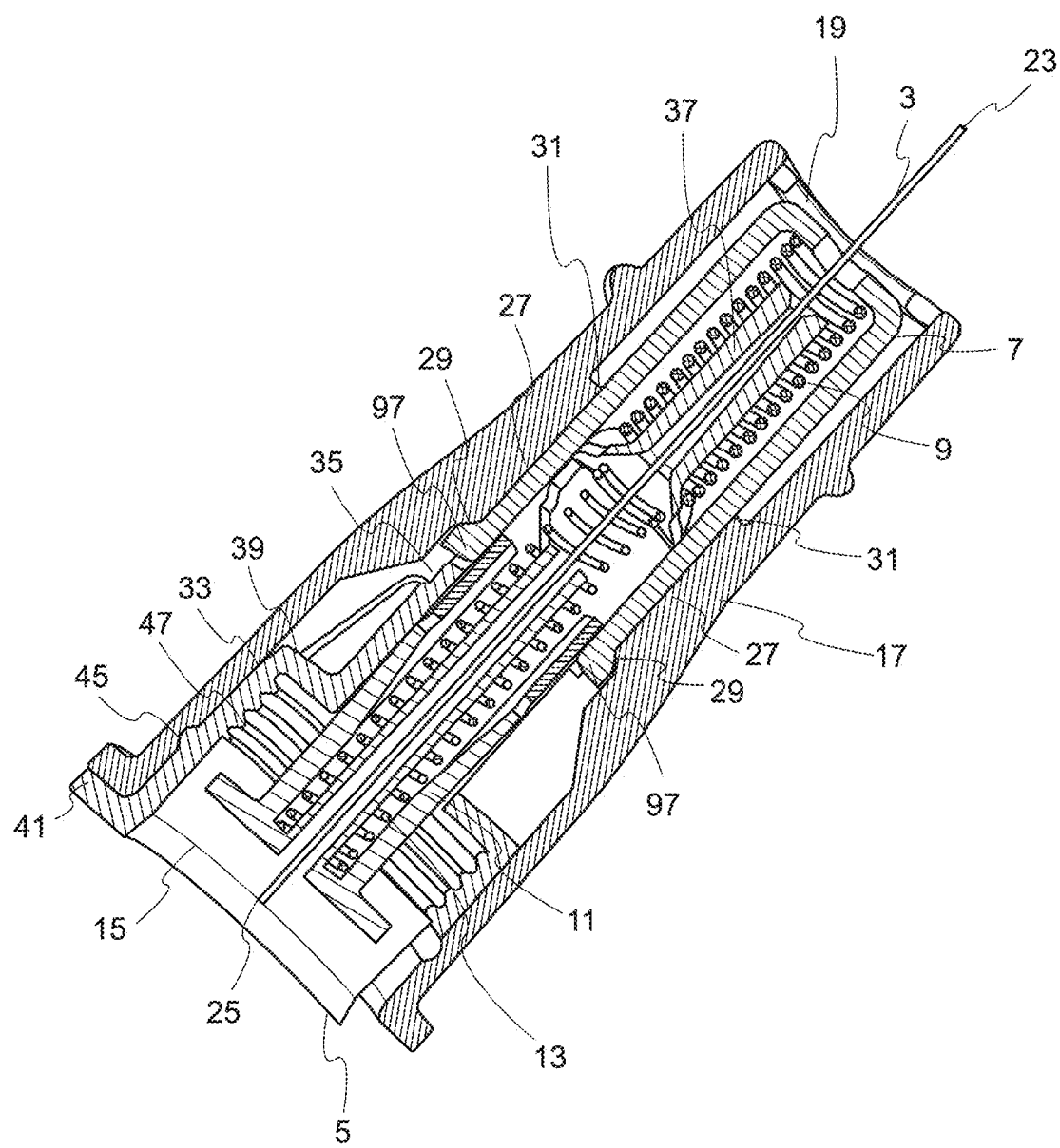
FIG. 4 is a cross-sectional view of the pen needle of FIG. 1 at ninety degrees to the view of FIG. 3.

FIGS. 1 to 6 illustrate a pen needle 1 in a pre-use state. The pen needle 1 comprises a needle 3, a needle carrier 5, a patient end (distal) needle shroud 7 and distal compression spring 9, a non-patient end (proximal) needle shroud 11 defining a proximal member, and proximal compression spring 13, a screw-threaded hub 15 and a housing 17.

The proximal (non-patient) end of the pen needle 1 is the end nearest to the medicament delivery device, typically a pen type injector. The distal (patient) end is the opposite end, furthest from the medicament delivery device.

Figure 5:
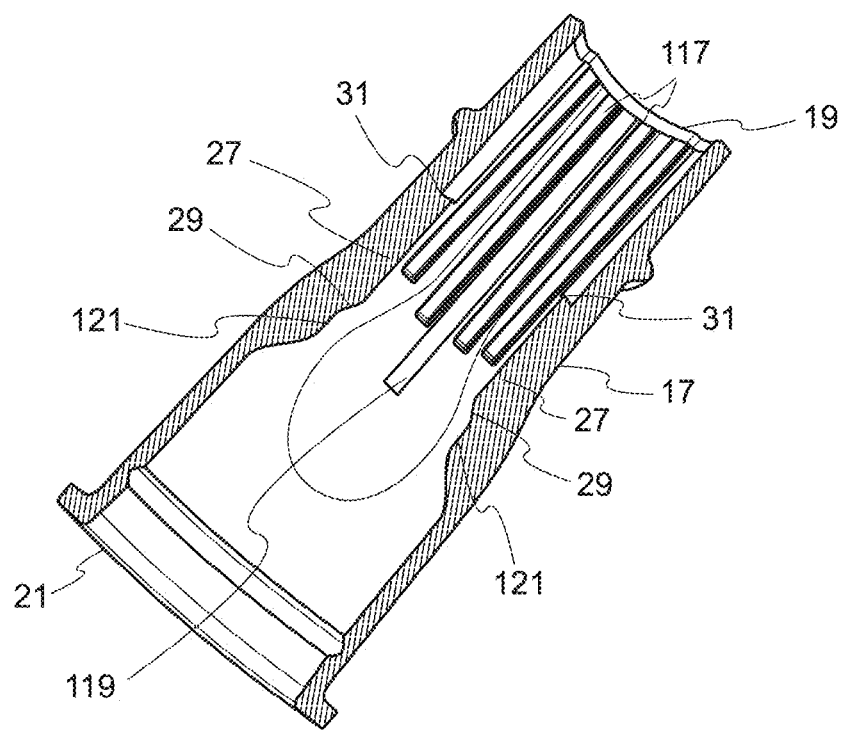
FIG. 5 is a cross-section view of the housing of the pen needle of FIG. 1.
Figure 6:
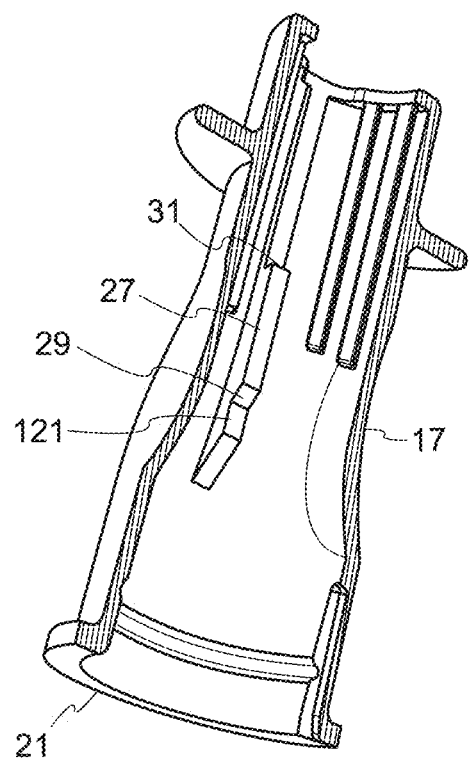
FIG. 6 is a cross-section view of the housing of the pen needle of FIG. 1 at ninety degrees to the view of FIG. 5.

The housing 17 is tubular, defining a central cavity with a generally cylindrical cross-section and with a patient (distal) end opening 19 at a distal end of the housing 17 and a non-patient (proximal) end opening 21 at a proximal end of the housing 17. A patient (distal) end 23 of the needle 3 extends outside of the housing 17 in a distal direction, through the patient end opening 19. The length of the exposed portion of the needle 3 that extends outside of the housing 17 is pre-determined and is chosen according to the desired depth to which the needle is to be inserted into a patient, for example the exposed portion may be 4 mm long. The non-patient (proximal) end 25 of the needle 3 does not extend past the non-patient end opening 21, it remains set back from the opening by a distance that is sufficient to reduce the risk of a needlestick injury. The housing 17 has a pair of needle shield guidance ribs 27, as best seen in FIGS. 5 and 6, aligned longitudinally and arranged diametrically opposite each other on the internal surface of the housing 17. The ribs 27 are each provided at a proximal end with a ramped deflector surface 29 and at a distal end with an abutment shoulder 31.

The needle carrier 5 is illustrated in detail in FIGS. 7 to 10. It, also, is tubular with a generally cylindrical cross-section. It has an external stepped profile that creates three adjoining sections that decrease in diameter along its longitudinal axis from its proximal end to its distal end. The section nearest to the proximal end is a collar 33 which is used to attach the needle carrier 5 to the housing 17. The middle section is a needle shroud guidance barrel 35 which constrains movement of the patient end needle shroud 7 and the non-patient end needle shroud 11. The distal section is a needle sleeve 37 which is used to hold the needle 3 in place relative to the needle carrier 5 by means of an adhesive located in an annular void between the internal surface of the needle sleeve 37 and the external surface of the needle 3.

Figure 9:
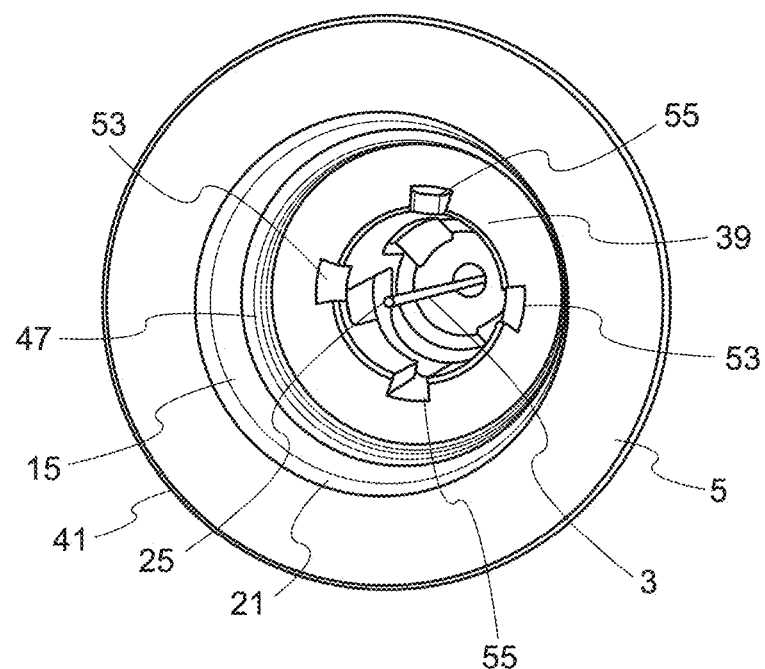
FIG. 9 is a close-up view of the inside of the collar of the needle carrier.
Figure 10:
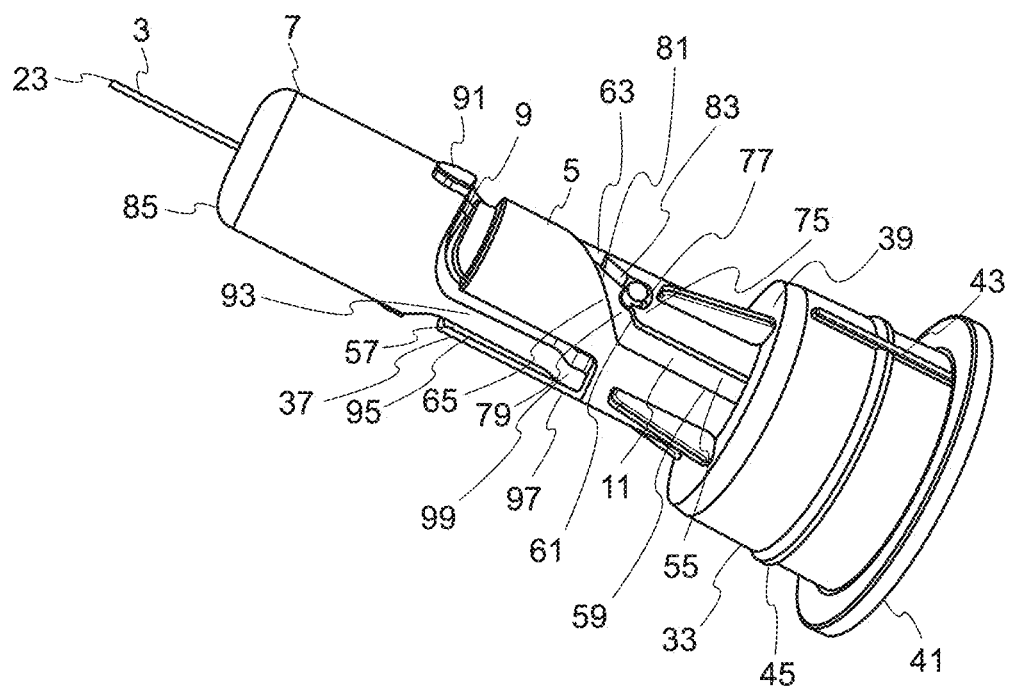
FIG. 10 shows the positions of the patient end needle shroud and the non-patient end needle shroud on the needle carrier in a pre-use state of the device.
Figure 18:
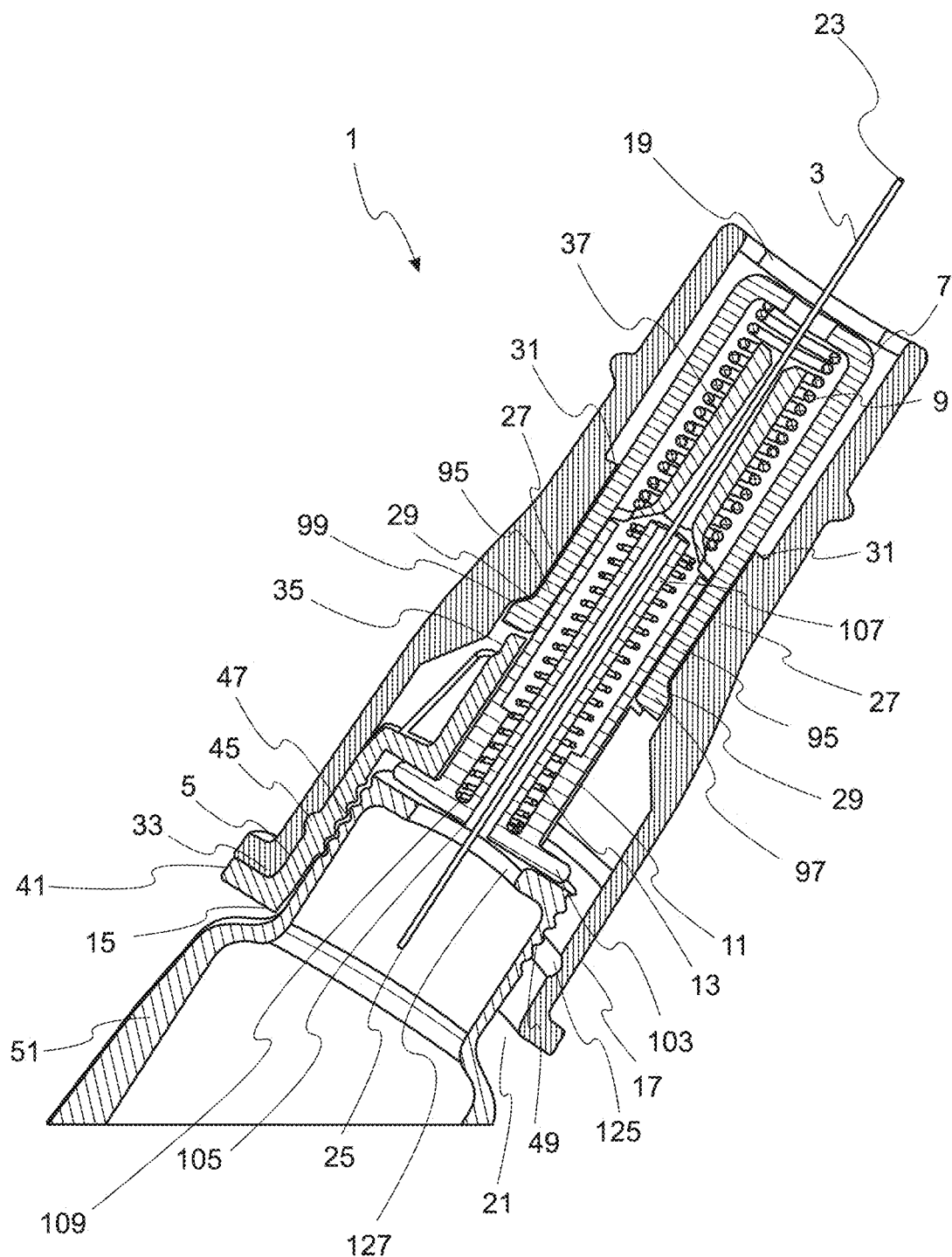
FIG. 18 is a cross-sectional view of the pen needle attached to the cartridge of a pen type drug delivery device and ready for an injection to be made.

The proximal section, collar 33, is joined to the intermediate section, i.e. needle shroud guidance barrel 35, at its distal end by an annular transverse plate 39. The proximal end of the collar 33 has a flange 41 with an external diameter that is larger than the external diameter of the collar 33 and that is approximately the same diameter as the external diameter of the housing 17 at its proximal end. Located on the external surface of the collar 33 are a longitudinal alignment rib 43 and an annular stop bead 45. The inside of the collar 33 is provided with a screw thread 47 that is complementary to a screw thread 49 provided on a cartridge housing 51 of a pen type drug delivery device (as shown in FIG. 18), to facilitate connection of the pen needle 1 to the cartridge housing 51. Also located inside the collar 33 and on the lip between the transverse plate 39 and the inside surface of the needle shroud guidance barrel 35 are two tongue deflection ramps 53 and two assembly slots 55, as shown in FIG. 9. The two tongue deflection ramps 53 are diametrically oppositely located on the lip, as are the two assembly slots 55, and they are all equally spaced around the lip.

Figures 7, 8:
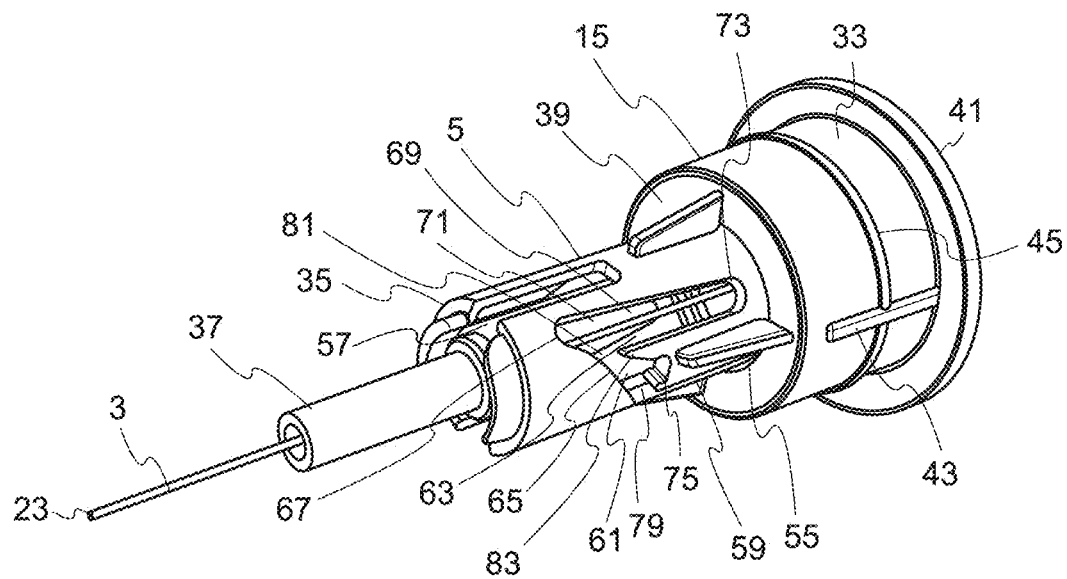
FIG. 7 is a perspective view of the needle carrier and needle.
FIG. 8 is a close-up view of the sub-assembly of the needle carrier and non-patient end needle shroud in a pre-use state.

The intermediate section, the needle shroud guidance barrel 35, has at its distal end and located within its wall a pair of guidance slots 57 for guiding movement of the patient end needle shroud 7. The guidance slots 57 extend longitudinally to approximately the mid-point of the needle shroud guidance barrel 35 and on diametrically opposite sides of it. Located within the wall of the needle shroud guidance barrel 35, towards its proximal end and on diametrically opposite sides of it, there is also a pair of continuous channels which together provide a means for assembling the non-patient end needle shroud 11 into the needle carrier 5 and for controlling its motion during use of the pen needle 1. Each continuous channel is formed from an axially extending assembly channel 59, a transition channel 61 and an axially extending locking channel 63 which in combination resemble an inverted 'U' formation when looked at in a plan view, with the patient end 23 of the needle 3 uppermost (for example as illustrated in FIG. 8). The assembly channel 59 forms the left hand side leg of the 'U', the transition channel 61 forms the bottom of the 'U' and the locking channel 63 forms the right hand leg of the 'U'. The assembly channel 59 runs in a longitudinal direction from the interface between the collar 33 and the needle shroud guidance barrel 35 to a point approximately mid-way along the length of the needle shroud guidance barrel 35, in line with the assembly slots 55. The transition channel 61 is slanted in an upwards direction from left to right (i.e. extends axially and azimuthally) and the distally located side of it is a track pin cam surface 65. A track pin recess 67 is located at the point at which the right hand end of the track pin cam surface 65 meets the locking channel 63. A part of the locking channel 63 is a track pin capture slot 69 which has a mouth 71 at its distal end that is relatively wide compared to the width of its blind end 73 which is at the proximal extremity of the locking channel 63. A first track portion with a track pin seat 75 is located adjacent to the transition channel 61, approximately mid-way between the intersections with the assembly channel 59 and the locking channel 63. The diameter of the transition channel 61 is narrowed on either side of the track pin seat 75, such that its width is slightly less than the diameter of the track pins 77. A first narrow 79 is located between the track pin cam surface 65 and the left hand edge of the track pin seat 75. A second narrow 81 is located between the track pin cam surface 65 and the tip of a finger 83 that extends longitudinally from the right hand edge of the track pin seat 75.

Figure 11:
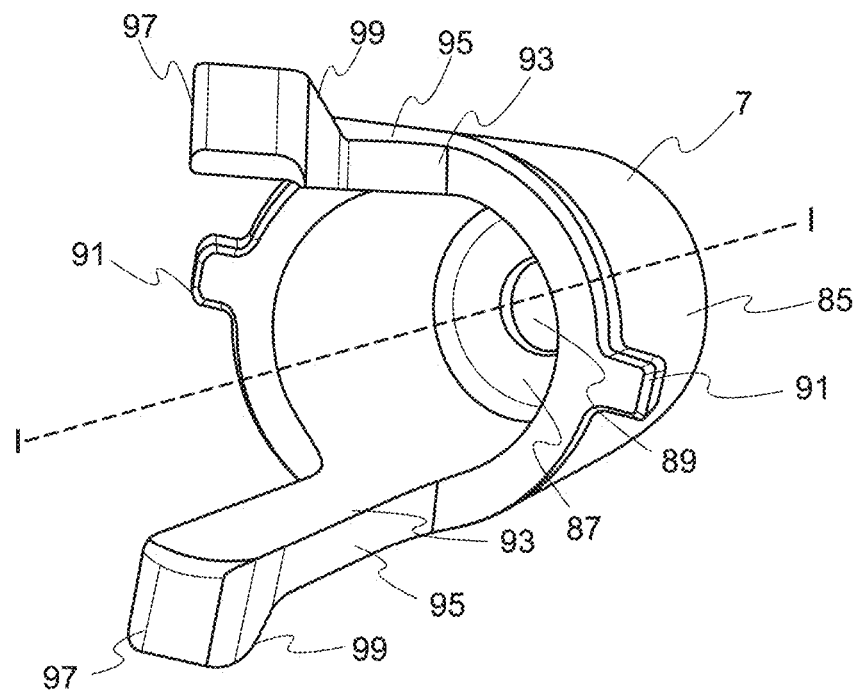
FIG. 11 shows the patient end needle shroud in perspective from the proximal end.

The patient end needle shroud 7 is illustrated in detail in FIG. 11. It is generally tubular, with a shroud portion 85. The shroud portion 85 has a circular cross-section and a partially closed distal end 87, with a circular needle aperture 89 located co-axially with the longitudinal axis H of the patient end needle shroud 7. Guidance bosses 91 are located adjacent to the proximal end of the shroud portion 85, on each side of the patient end needle shroud 7. The guidance bosses 91 extend radially outwardly from the external surface of the shroud portion 85. The shroud portion 85 also has a pair of deformable locating formations in the form of flexible lock-out legs 93, attached to the proximal end of the shroud portion 85 and diametrically opposed on each side of the patient end needle shroud 7. The flexible lock-out legs 93 extend longitudinally outwardly from the proximal end of the shroud portion 85, in line with the external surface of the shroud portion 85 and as an extension of it and are equally spaced with the guidance bosses 91 around the circumference of the shroud portion 85. The flexible lock-out legs 93 have a stem 95 and a retention head 97. Each retention head 97 has a ramped external surface 99 on its radially outwardly directed face.

Figure 12:
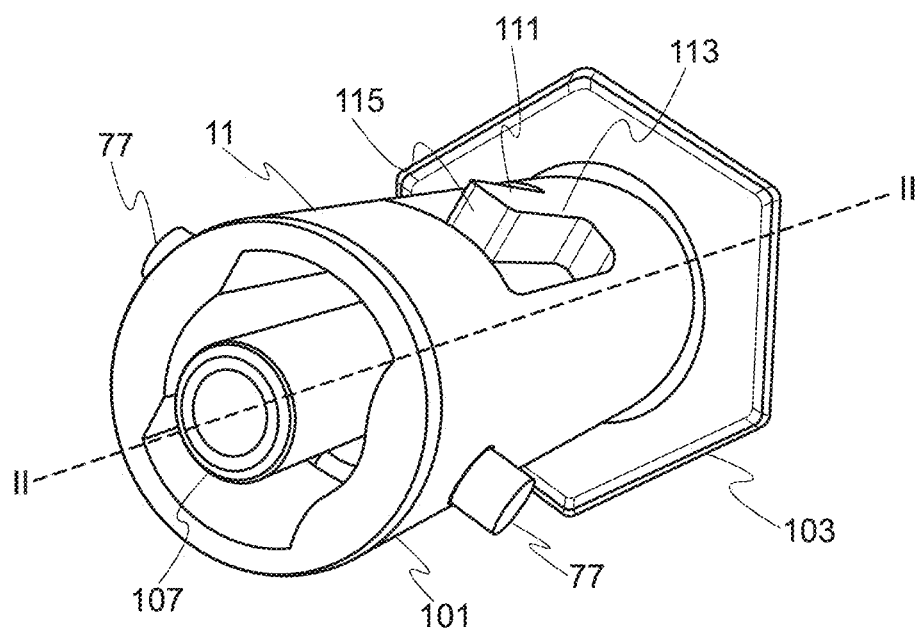
FIG. 12 shows the non-patient end needle shroud in perspective from the distal end.
Figure 13:
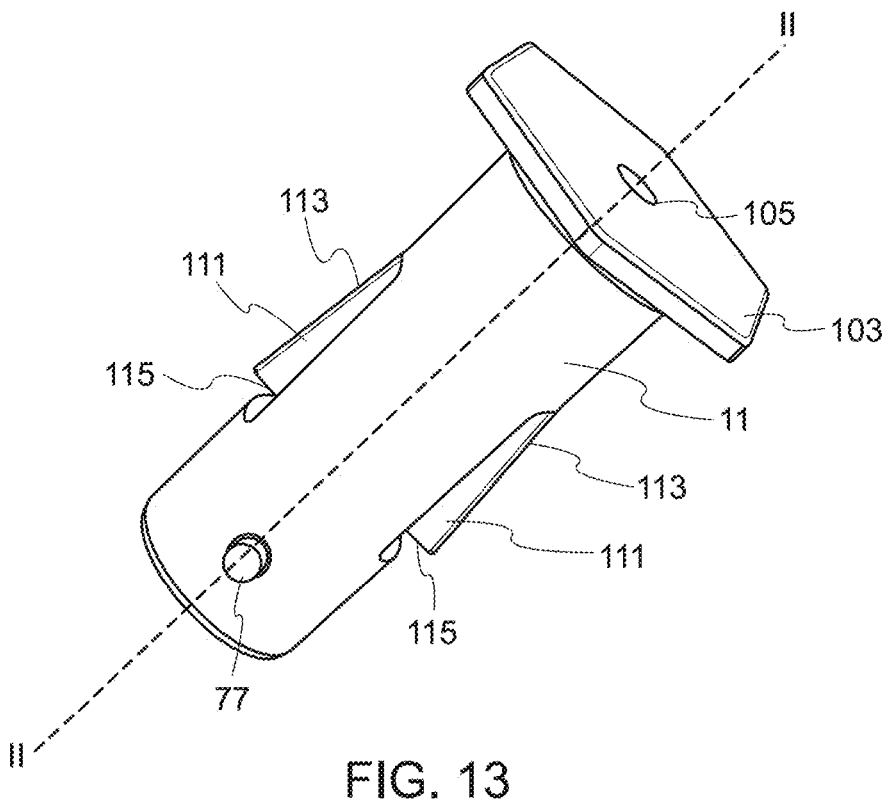
FIG. 13 shows the non-patient end needle shroud in perspective from the proximal end.

The non-patient end needle shroud 11 is illustrated in detail in FIGS. 12 and 13. It is also generally tubular, with a shroud portion 101 that has a circular cross-section. An actuator plate 103 is formed at the proximal end of the shroud portion 101. The actuator plate 103 is sized to fit within the collar 33, so that it can be moved axially relative to the needle carrier 5. The actuator plate 103 has at least a portion with a transversal width that is larger than the internal diameter of the screw threaded pen needle attachment portion of a cartridge housing 51, to which the pen needle 1 is intended to be fitted. The actuator plate 103 has a circular needle aperture 105 located co-axially with the longitudinal axis II-II of the non-patient end needle shroud 7. A spring guidance tube 107 extends in a distal direction from the distal side of the actuator plate 103 past the end of the shroud portion 101 and is co-axially aligned with the longitudinal axis II-II. The internal diameter of the spring guidance tube 107 is larger than the external diameter of the needle 3. The external diameter of the spring guidance tube 107 is smaller than the internal diameter of the proximal spring 13. The spring guidance tube 107 extends outside of the shroud portion 101. The annular surface between the external circumference of the spring guidance tube 107 and the internal circumference of the shroud portion 101 provides a proximal spring seat 109 for the proximal spring 13. Located at diametrically opposite positions on the shroud portion 101 are flexible lock-out tongues 111. The lock-out tongues 111 are provided in the wall of the shroud portion 101, between its proximal and distal ends. The radially external surface of each lock-out tongue 111 has a biasing surface 113 between its proximal and distal ends. Each lock-out tongue 111 is fixed at its proximal end to the shroud portion 101 and at its distal end it is free to move and has an abutment surface 115. Each lock-out tongue 111 is biased outwardly such that in the absence of any externally radially applied force the biasing surface 113 extends outwardly at an oblique angle from the external surface of the shroud portion 101, such that the abutment surfaces 115 extend at least partially outside of the shroud portion 101 in a radial direction. Track pins 77 are located adjacent to the distal end of the shroud portion 101 at diametrically opposite positions. The track pins extend radially outwardly and have a circular cross-section. The lock-out tongues 111 and the track pins 77 are equally spaced around the circumference of the shroud portion 101.

Figure 14:
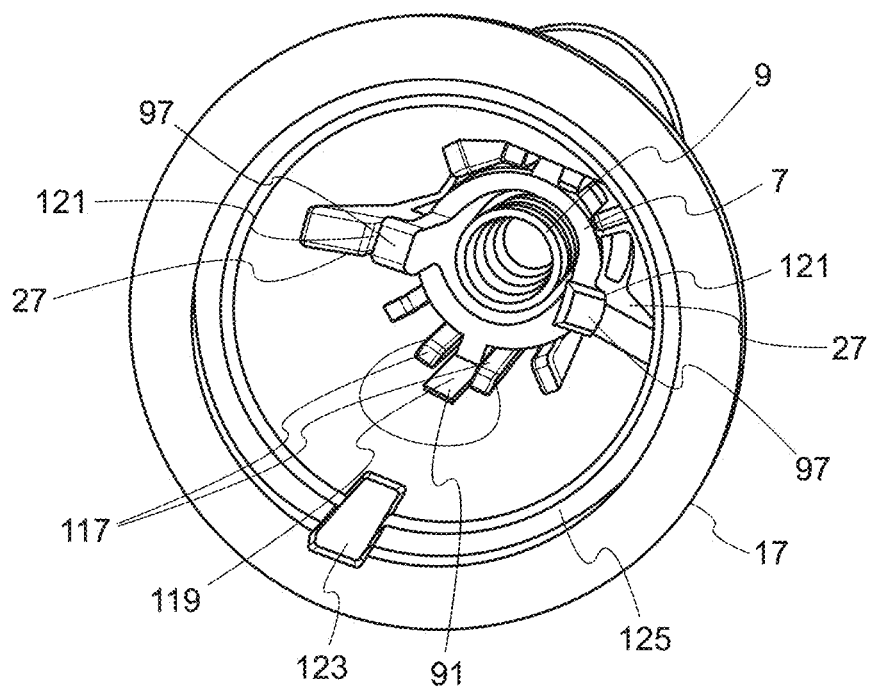
FIG. 14 is a perspective view of the housing from the proximal end and showing the orientation of the patient end needle shroud and distal spring in the housing in a pre-use state.

The first step in assembly of the pen needle 1 is to locate the patient end needle shroud 7 into the housing 17, as illustrated in FIG. 14. The housing 17 is provided on its internal surface with two pairs of longitudinally aligned, diametrically oppositely located, boss guiding ribs 117, each pair of which ribs 117 defining between them a boss guiding channel 119. Two diametrically oppositely located ramped retention head abutment surfaces 121 are also provided on the internal surface of the housing 17. The boss guiding channels 119 and the retention head abutment surfaces 121 are equally spaced around the internal circumference of the housing 17. A guiding boss 91 is located within the boss guiding channel 119 when the patient end needle shroud 7 is located within the housing 17. The ramped surfaces 99 of the retention heads 97 of the lock-out legs 93 are brought into abutment with the retention head abutment surfaces 121. Thus movement of the patient end needle shroud 7 relative to the housing 17 is prevented in a rotational direction by the boss guiding channels 119 and in an axial direction by the retention head abutment surfaces 121.

The second step is to locate the distal spring 9 inside the housing 17 and in particular to seat it within the patient end needle shroud 7. The internal proximally facing surface of the shroud portion 85 acts as a distal spring seat for the distal spring 9.

Figure 15:
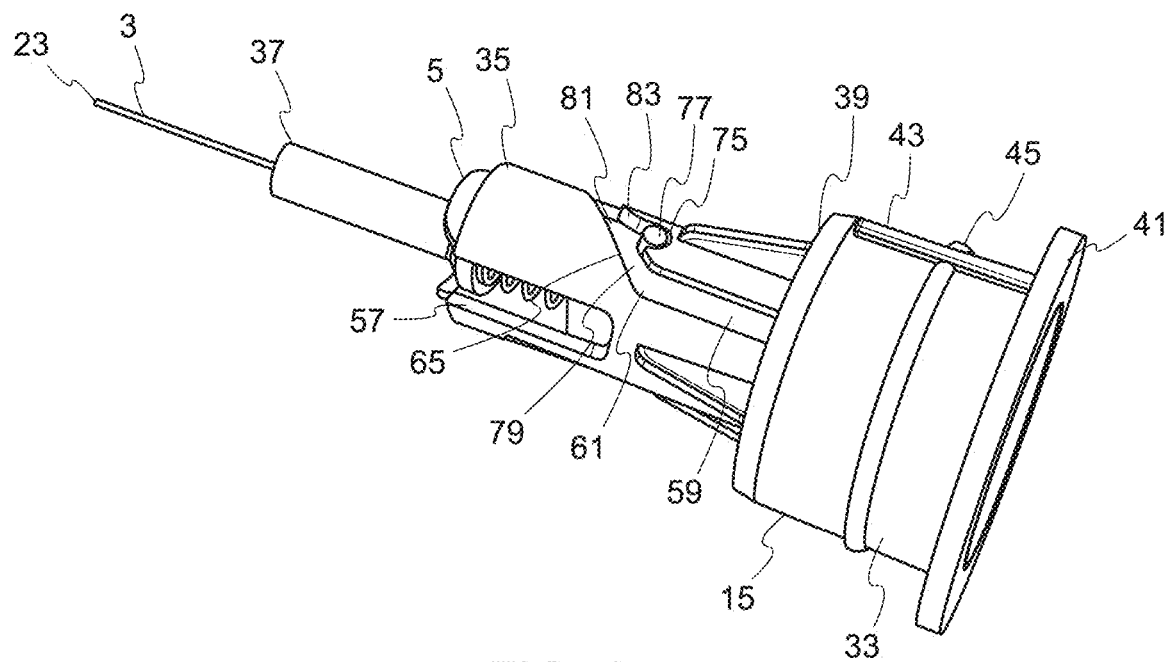
FIG. 15 is a perspective view of the sub-assembly that comprises the needle carrier, needle, proximal spring and non-patient end needle shroud in a pre-use state viewed from the proximal end.
Figure 16:
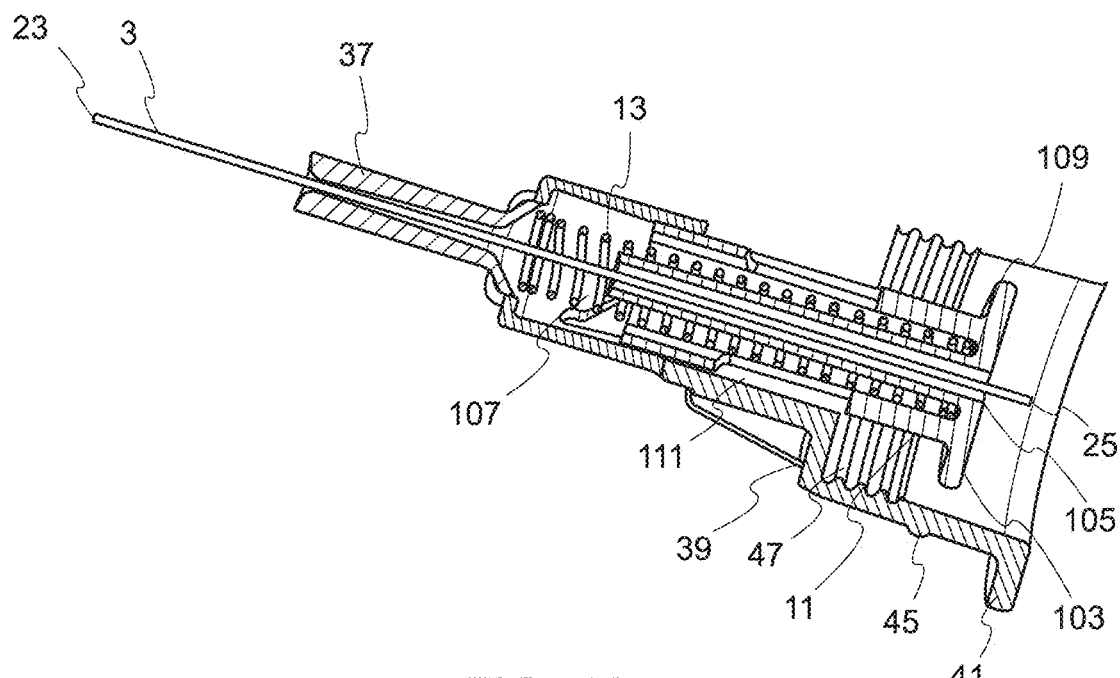
FIG. 16 is a cross-section view of the sub-assembly of FIG. 15.
Figure 17:
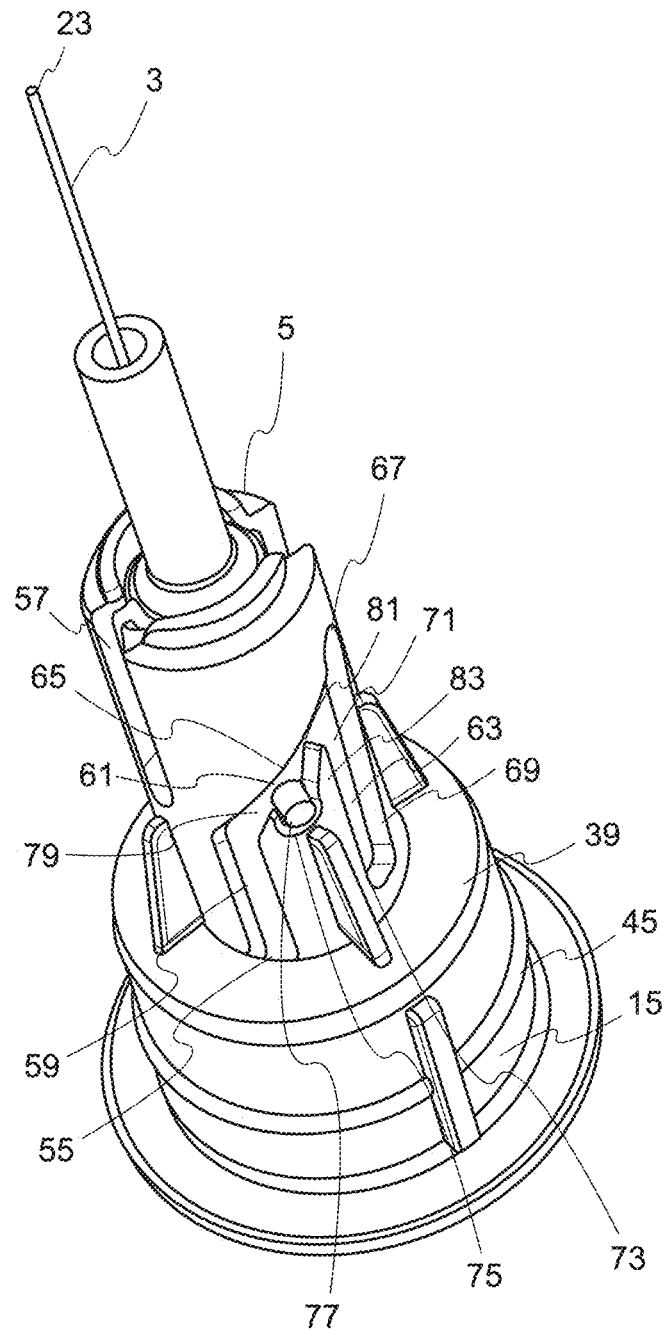
FIG. 17 is a perspective view of the sub-assembly of FIG. 15.

The third step is to create a sub-assembly from the needle 3, needle carrier 5, proximal spring 13 and non-patient end needle shroud 11. The sub-assembly is illustrated in FIGS. 15, 16 and 17. The needle 3 is fixed into the needle sleeve 37 using an adhesive. The proximal spring 13 is located around the spring guidance tube 107 of the non-patient end needle shroud 11 and seated on the proximal spring seat 109. The free length of the proximal spring 13 is longer than the spring guidance tube 107. The non-patient end needle shroud 11 is co-axially aligned with the needle carrier 5 and rotated to a position in which each of the two track pins 77 is aligned with an assembly slot 55 and an assembly channel 59 and each of the two flexible lock-out tongues 111 is aligned with a tongue deflection ramp 53. The non-patient end needle shroud 11 is then inserted axially into the needle carrier 5, each track pin 77 passes through an assembly slot 55 and enters an assembly channel 59 and the biasing surface 113 of each flexible lock-out tongue 111 engages with a tongue deflection ramp 53 such that each lock-put tongue 111 is deflected radially inwardly, to assume an orientation that allows it to enter the needle shroud guidance barrel 35. The non-patient end needle shroud 11 is moved axially forwards and when each of the track pins 77 contacts a track pin cam surface 65 the inclined orientation of the track pin cam surface 65 causes the non-patient end needle shroud 11 to rotate in a clockwise direction, when viewed from the proximal end of the safety pen needle, so that the track pin 77 enters the transition channel 61. Axial movement of the non-patient end needle shroud is ceased when each of the track pins 77 is longitudinally aligned with a track pin seat 75. The force applied to the non-patient needle shroud 11 by the assembly equipment to cause its distally directed axial movement is then removed and the non-patient end needle shroud 11 is then moved in a proximal axial direction by a force provided by the proximal spring 13, so that each of the track pins 77 is seated within a track pin seat 75 (first position). In order to align the track pins 77 within the track pin seats 75 the track pins 77 must be forced through the first narrow 79. A moderate assembly force is sufficient to deflect the respective parts of the needle carrier 5 to open up the narrow 79 so that the track pins 77 can pass through.

The fourth step is to locate the needle carrier sub-assembly within the housing 17. The needle carrier sub-assembly is rotated until the longitudinal alignment rib 43 is aligned with a rib alignment channel 123 provided in the housing 17, the inter-engaging formations locating the carrier against rotation. The needle carrier 5 and the housing 17 are then brought together axially until the axial movement is arrested when the annular stop bead 45 snap-fits into annular stop channel 125, the inter-engaging formations locating the carrier axially in the housing.

Finally, the pen needle 1 is placed in a primary container, typically a complementarily shaped plastics container (not shown) that is provided with a foil seal in order to maintain the sterility of the pen needle 1 before use.

Figure 19:
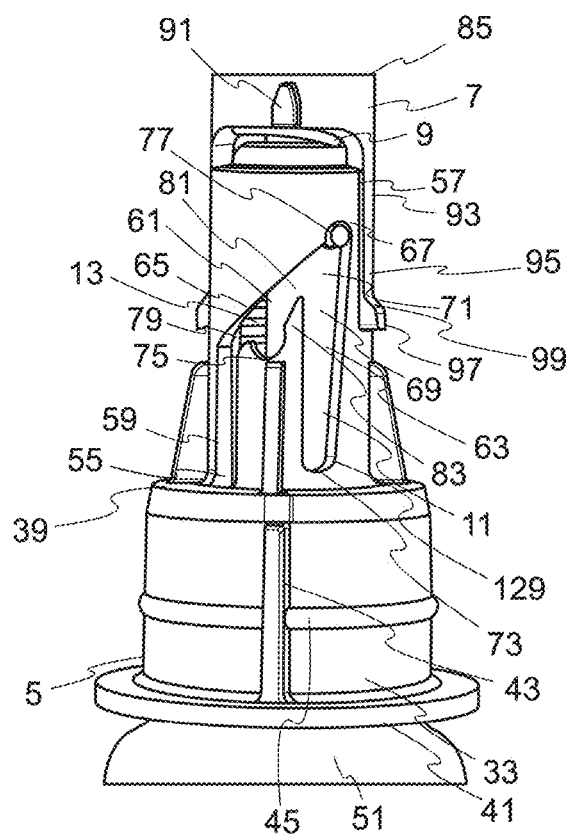
FIG. 19 is a view of the position of the non-patient end needle shroud relative to the needle carrier when the pen needle is attached to the cartridge housing of a pen type drug delivery device (with housing omitted for clarity).
Figure 20:
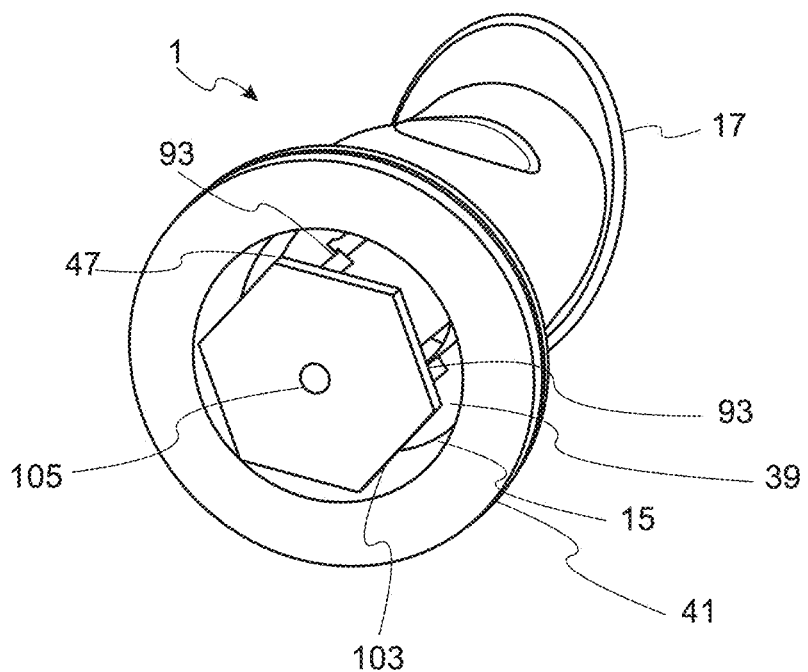
FIG. 20 is a perspective view from a proximal end of the pen needle after use.

A typical use of a pen needle 1 is for the delivery of a drug from a medicament cartridge of a pen type drug delivery device. FIG. 18 shows the pen needle 1 fitted to a cartridge housing 51 by means of screw threads 47 and 49 respectively. The cartridge housing 51 has an annular end face 127 at its distal end which contacts the actuator plate 103 of the pen needle. The cartridge housing 51 is advanced into the pen needle 1 as it is screwed in, at a certain point its end face 127 contacts the actuator plate 103 and causes the non-patient end needle shroud 11 to move axially in a distal direction. The track pins 77 contact the track pin cam surfaces 65 and cause the non-patient end needle shroud 11 to rotate in a clockwise direction, when viewed from the proximal end of the pen needle 1. The rotation continues until axial movement of the actuator plate 103 stops when the distal face of the actuator plate 103 contacts the proximal face of the annular transverse plate 39. The track pins 77 are each located at that point within a track pin recess 67, as shown in FIG. 19. In order to locate the track pins 77 within the track pin recesses 67 the track pins 77 must be forced through the second narrow 81. The force applied to the pen needle 1 by the user when they are screwing it on to the cartridge housing 51 is sufficient to deflect the finger 83 to open up the narrow 81 so that the track pins 77 can pass through. When the pen needle 1 has been fully engaged with the cartridge housing 51 the needle 3 has pierced the septum of a cartridge (not shown) and an injection of the medicament can be delivered to the patient. When the injection has been completed the pen needle 1 is removed from the cartridge housing 51 to allow it to be placed in a bin for disposal. The action of unscrewing the pen needle 1 from the cartridge housing causes the patient end needle shroud 7 and the non-patient end needle shroud 11 to be deployed, such that the respective patient end of the needle 23 and non-patient end of the needle 25 are covered, in order to prevent needle-stick injuries.

The operation of the non-patient end needle shroud 11 will be described first. Unscrewing the pen needle 1 from the cartridge housing 51 allows the non-patient end needle shroud 11 to be driven in a proximal direction by the force from the proximal spring 13. The track pins 77 move in a proximal direction in a second track portion and the motion control track 129 guides their movement, such that they do not move towards the transition channel 61. The mouth 71 assists with the guidance of the track pins 77. In any case, the second narrow 81 prevents the track pins 77 from passing back into the transition channel 61, because the width of the neck is less than the diameter of the track pins 77 and the force provided by the proximal spring 13 is insufficient to deflect the finger 83. The track pins 77 rest in the blind ends 73 once the pen needle 1 has been unscrewed from the cartridge housing 51, thus limiting the proximal movement of the non-patient end needle shield 11.

Figure 21:
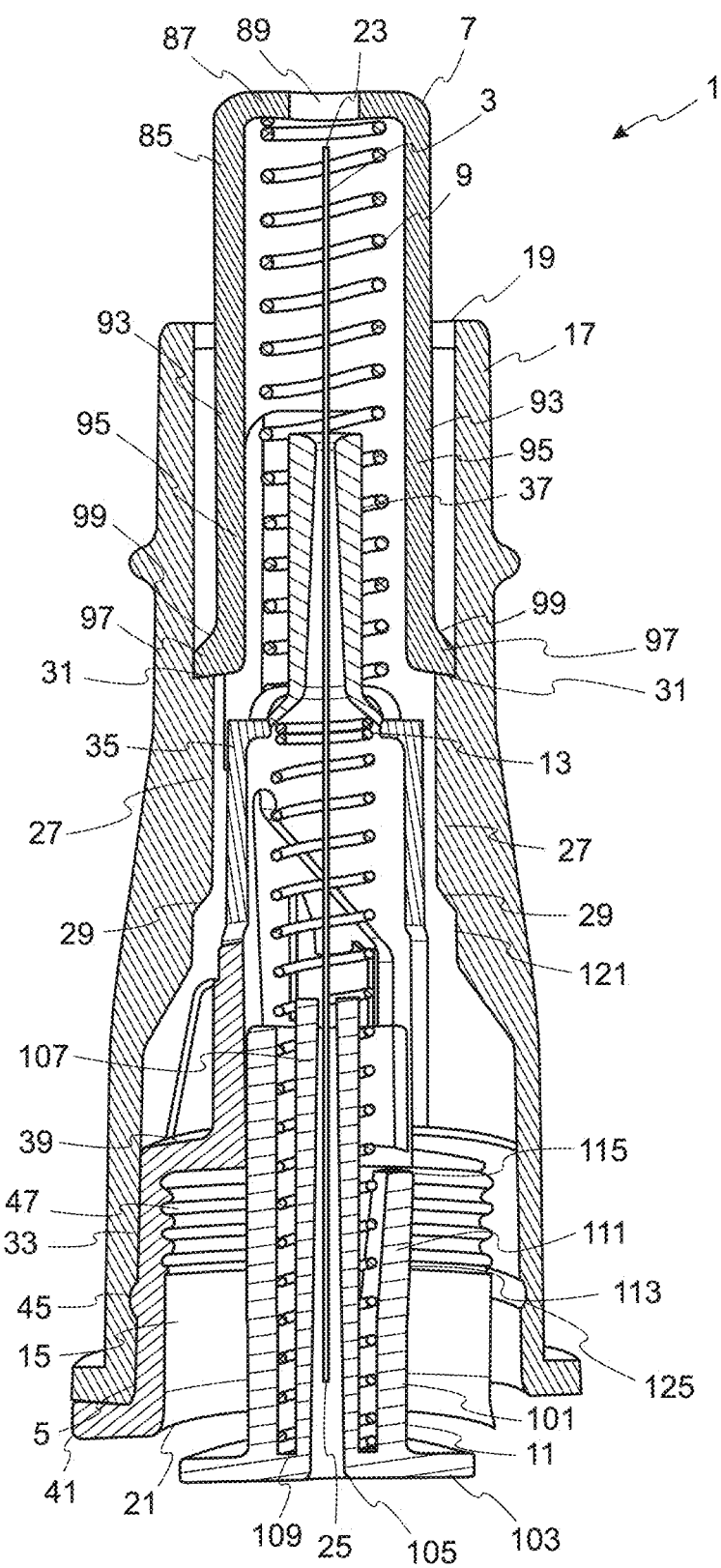
FIG. 21 is a cross-sectional view of the pen needle after use.

Simultaneous with the movement of the track pins 77, the lock-out tongues 111 move axially in a proximal direction relative to the needle carrier 5. When the abutment surfaces 115 move past the annular transverse plate 39, the lock-out tongues 111 move radially outwards, so that the distance between the two most radially outwards points of the lock-out tongues 111 is greater than the internal diameter of the needle shroud guidance barrel 35. The non-patient end needle shroud 11 cannot then be pushed back in an axial direction by a distance sufficient to uncover the non-patient end 25 of the needle 3 because the rotation of the non-patient end needle shroud 11 has caused the lock-out tongues 111 to move out of alignment with the tongue deflection ramps 53. Instead the abutment surfaces 115 provided on the lock-out tongues 111 engage and latch with the proximal face of the annular transverse plate 39 of the needle carrier 5, so that there can be no axial movement in a distal direction (FIG. 21).

Figure 22:
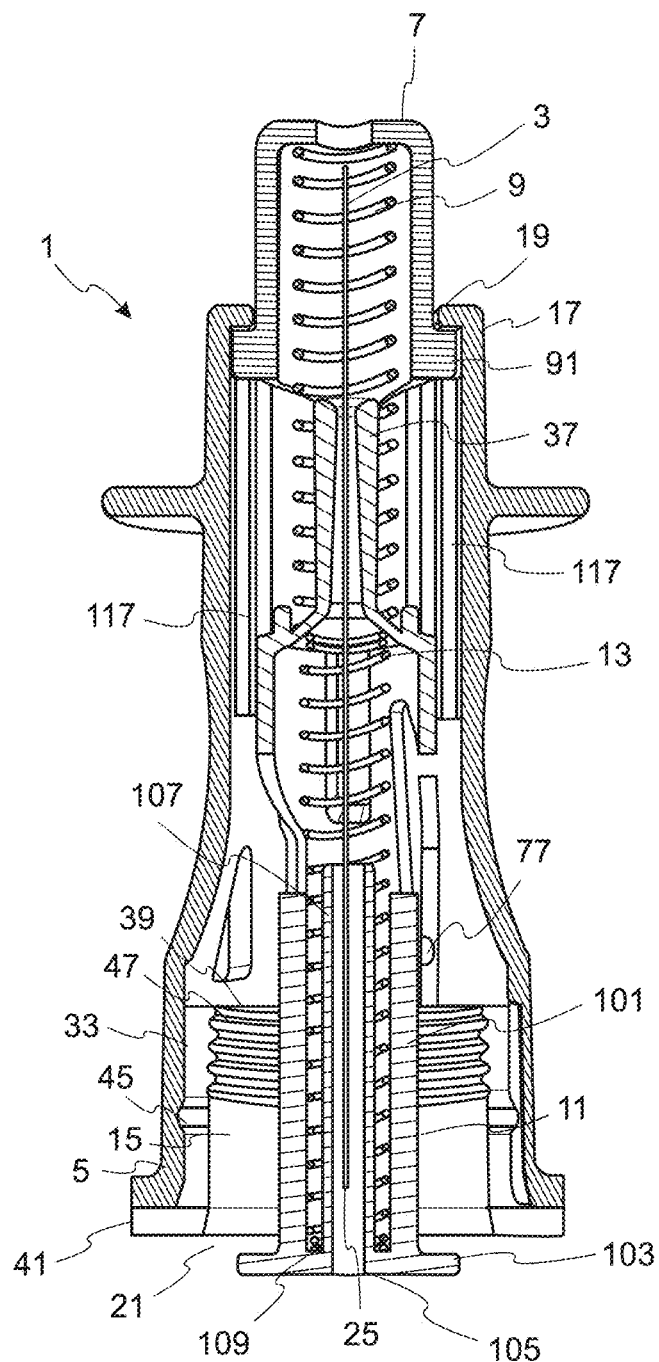
FIG. 22 is a cross-sectional view of the pen needle after use at 90 degrees to the view of FIG. 21.

Operation of the patient end needle shroud 7 is driven by the distal spring 9. The movement of the non-patient end needle shroud 11 in a proximal direction from its first position to a second position has withdrawn the spring guidance tube 107 from its previous position between the flexible lock-out legs 93 of the patient end needle shroud 7, such that the flexible lock-out legs 93 are able to flex. The force applied to the patient end needle shroud 7 by the distal spring 9 causes the flexible lock-out legs 93 to flex radially inwardly as a result of interaction of the ramped surfaces 99 on the retention heads 97 with the ramped deflector surfaces 29 on the inside of the housing 17. The radially inwards movement of the flexible lock-out legs 93 allows the needle shroud 7 to move axially forwards (distally) until guidance boss formations 91 reach the distal, blind, ends of the boss guiding channel formations 119 in the housing 17, thereby limiting any further distal movement (FIG. 22). The retention heads 97 pass the needle shield guidance ribs 27 and thus the flexible lock-out legs 93 expand radially outwardly. If a force is applied to the patient end needle shroud 7 in a proximal direction then the retention heads 97 will each come into abutment with an abutment shoulder 31 on the needle shroud guidance ribs 27, thereby preventing exposure of the patient end 23 of the needle 3 and thereby guarding against a needlestick injury.

It is sometimes the case that a user may not fully screw the pen needle 1 on to the cartridge housing 51. The pen needle 1 of the present invention has a geometry that can cope with a situation in which the pen needle 1 is only partially screwed on to the cartridge housing 51. The length of the non-patient end needle shroud 11 is selected so that if even if the user only screws the pen needle 1 onto the cartridge housing body 41 for one revolution, the track pins 77 will move out of the transition channel 61 and into the locking channel 63. In such a scenario the track pins 77 would not be located within the track pin recesses 67, but upon unscrewing of the pen needle 1 from the cartridge housing 51 the track pins 77 would move towards the blind end 73 of the locking channel 63, guided by the motion control track 129, in the usual manner.

If the pen needle 1 is pushed onto a cartridge housing 51, but the screw threads 47 and 49 are not engaged, then the non-patient end needle shroud 11 will only have been moved forwards axially in a distal direction by an extent such that the track pins 77 will remain within the transition channel 61. If the user then removes the pen needle 1 from the cartridge housing 51, for example because they have changed their minds about making an injection, then the non-patient end needle shroud 11 will return to its pre-use state, with the track pins 77 returning to the track pin seats 75, ready for future use.

Accidental disassembly of the pen needle 1 or deployment of the patient and non-patient end needle shrouds 7 and 11 is prevented because the forces associated with such accidental acts are not sufficient to push the track pins 77 through either the first narrow 79 or the second narrow 81.

The configuration of the non-patient end needle shroud/proximal shroud 11 (proximal member) means that actuation of the patient end shroud/distal shroud 7 can be effected by removal of the cartridge housing 51, thus providing a way to avoid some of the problems associated with other designs.

REFERENCE SIGNS LIST 1 pen needle
3 needle
5 needle carrier
7 patient end needle shroud
9 distal spring
11 non-patient end needle shroud
13 proximal spring
15 hub
17 housing
19 patient end opening
21 non-patient end opening
23 patient end of needle
25 non-patient end of needle
27 needle shroud guidance rib
29 ramped deflector surface
31 abutment shoulder
33 collar
35 needle shroud guidance barrel
37 needle sleeve
39 annular transverse plate
41 collar flange
43 longitudinal alignment rib
45 annular stop bead
47 screw thread
49 screw thread
51 cartridge housing
53 tongue deflection ramp
55 assembly slot
57 guidance slot
59 assembly channel
61 transition channel
63 locking channel
65 track pin cam surface
67 track pin recess
69 track pin capture slot
71 mouth
73 blind end
75 track pin seat
77 track pin
79 first narrow
81 second narrow
83 finger
85 shroud portion
87 partially closed distal end
89 circular needle aperture
91 guidance boss
93 flexible lock-out leg
95 stem
97 retention head
99 ramped surface
101 shroud portion
103 actuator plate
105 circular needle aperture
107 spring guidance tube
109 proximal spring seat
111 lock-out tongue
113 biasing surface
115 abutment surface
117 boss guiding rib
119 boss guiding channel
121 retention head abutment surface
123 rib alignment channel
125 annular stop channel
127 annular end face
129 motion control track
130 shield

The invention claimed is:

1. A pen needle comprising:
a housing defining a central cavity with a distal end having a distal opening and a proximal end having a proximal opening;
a needle carrier located within the central cavity and supporting a needle that extends through the central cavity such that a distal end of the needle projects from the distal end of the cavity through the distal opening;
a distal shroud positioned around the needle and located within the central cavity and at the distal end of the central cavity, the distal shroud including formations that, when engaged with the housing, limit axial movement of the distal shroud in a distal direction;
a distal compression spring positioned around the needle and located between the needle carrier and the distal shroud, wherein the distal compression spring acts to urge the distal shroud away from the needle carrier towards the distal opening; and
a proximal member located within the central cavity at the proximal end;
wherein the proximal member is movable in use between a first position, in which a distal end of the proximal member engages a proximal end of the distal shroud to hold the formations in the engagement with the housing, and a second position in which the proximal member is closer to the proximal opening and the distal end of the proximal member is not engaged with the proximal end of the distal shroud such that the formations are movable out of the engagement with the housing and the distal shroud is movable in the distal direction by the distal compression spring to project from the distal opening and to surround the distal end of the needle projecting from the distal opening.

2. The pen needle as claimed in claim 1, wherein a proximal end of the housing has formations for connecting a cartridge housing to the pen needle, wherein, when connected, the cartridge housing holds the proximal member in the first position, and when disconnected, allows the proximal member to move to the second position.

3. The pen needle as claimed in claim 1, wherein the proximal member comprises a proximal shroud positioned around the needle and located within the central cavity and at the proximal end of the central cavity.

4. The pen needle as claimed in claim 3, wherein the pen needle further comprises a proximal compression spring positioned around the needle and located between the needle and the proximal shroud, wherein the proximal compression spring acts to urge the proximal shroud away from the needle carrier towards the proximal opening;
wherein the proximal shroud is movable by the proximal compression spring between the first position and the second position.

5. The pen needle as claimed in claim 3, wherein a distal end of the proximal shroud engages in the proximal end of the distal shroud in the first position to hold the formations in the engagement with the housing, and wherein the distal end of the proximal shroud is not engaged in the proximal end of the distal shroud in the second position, such that the formations are movable out of the engagement with the housing.

6. The pen needle as claimed in claim 3, wherein a proximal end of the needle is located within the proximal shroud when the proximal shroud is in the second position.

7. The pen needle as claimed in claim 6, wherein, in the first position of the proximal shroud, the proximal end of the needle projects beyond a proximal end of the proximal shroud by a length that is less than a length of a distal end of the proximal shroud engaged with the proximal end of the distal shroud.

8. The pen needle as claimed in claim 3, wherein the proximal shroud includes a latch for holding the proximal shroud in the second position.

9. The pen needle as claimed in claim 3, wherein the proximal shroud comprises an actuator plate at a proximal end of the proximal shroud by which force can be applied to the proximal shroud to rotate the proximal shroud within the housing and to move the proximal shroud axially against a proximal compression spring.

10. The pen needle as claimed in claim 3, wherein the proximal shroud engages the needle carrier by means of a pin and track arrangement, the pin and track arrangement comprising a pin and a track, such that rotation of the proximal shroud relative to the needle carrier moves the pin from a first portion of the track in which the proximal shroud is held in the first position against a proximal compression spring, to a second portion of the track in which the proximal shroud is axially movable to the second position by the proximal compression spring.

11. The pen needle as claimed in claim 10, wherein the pin and track arrangement comprises the pin on an outer surface of the proximal shroud and the track formed in a wall of the needle carrier.

12. The pen needle as claimed in claim 11, wherein the track in the wall of the needle carrier comprises a pin seat defining the first portion of the track, and a transition channel extending axially and azimuthally along the wall of the needle carrier from the first portion of the track to the second portion of the track extending axially along the wall of the needle carrier.

13. The pen needle as claimed in claim 12, wherein the track further comprises an assembly channel extending axially along the wall of the needle carrier to connect to the transition channel on an opposite side of the pin seat to the second portion of the track.

14. The pen needle as claimed in claim 3, wherein the proximal shroud comprises an actuator plate and wherein the proximal opening of the proximal end of the central cavity includes an internal screw thread by means of which a cartridge housing can be attached, such that screwing the cartridge housing onto the housing applies axial and rotational force to the actuator plate.

15. The pen needle as claimed in claim 1, wherein the housing includes formations which comprise ramped internal surfaces and wherein the formations on the distal shroud comprise deformable formations having ramped external surfaces that are engageable with the corresponding ramped internal surfaces on the housing; an action of the distal compression spring causing the deformable formations to deform and disengage from the formations in the housing when the distal end of the proximal member is disengaged from the proximal end of the distal shroud.

16. The pen needle as claimed in claim 1, wherein the distal shroud comprises further formations that are engageable with distal end formations in the housing to prevent disengagement of the distal shroud from the housing when moved in the distal direction by the distal compression spring to project from the distal opening and to surround the distal end of the needle projecting from the distal opening.

17. The pen needle as claimed in claim 1, wherein the housing includes internal formations that engage the needle carrier to locate the needle carrier axially and rotationally.

18. A method of using the pen needle as claimed in claim 1, the method comprising:
   with the proximal member in the first position, connecting a cartridge housing to a proximal end of the housing so as to engage a proximal end of the proximal member; and
   disconnecting the cartridge housing from the proximal end of the housing, thereby releasing the proximal member so as to disengage the distal end of the proximal member from the proximal end of the distal shroud thereby releasing the formations to move out of the engagement with the housing and moving the distal shroud in the distal direction by the distal compression spring to project from the distal opening and to surround the distal end of the needle projecting from the distal opening.

19. The method of using the pen needle as claimed in claim 18, wherein the proximal member comprises a proximal shroud positioned around the needle and located within the central cavity and at the proximal end of the central cavity, the method further comprising:
   with the proximal shroud in the first position, connecting the cartridge housing to the proximal end of the housing so as to engage a proximal end of the proximal shroud and to rotate the proximal shroud in the housing and move the proximal shroud axially against a proximal compression spring; and
   disconnecting the cartridge housing from the proximal end of the housing, thereby releasing the proximal compression spring to move the proximal shroud to the second position to initially surround a proximal end of the proximal compression spring, and to subsequently disengage a distal end of the proximal shroud from the proximal end of the distal shroud thereby releasing the formations to move out of the engagement with the housing and moving the distal shroud in the distal direction by the distal compression spring to project from the distal opening and to surround the distal end of the needle projecting from the distal opening.

\* \* \* \* \*